United States Patent [19]

Biver

[11] 4,105,411
[45] Aug. 8, 1978

[54] DEVICE FOR DETERMINING THE ACTIVATED CLOTTING TIME OF A BLOOD SAMPLE

[75] Inventor: William Ralph Biver, Dubuque, Iowa
[73] Assignee: Sybron Corporation, Rochester, N.Y.
[21] Appl. No.: 829,297
[22] Filed: Aug. 31, 1977
[51] Int. Cl.² .................................................. G01N 33/16
[52] U.S. Cl. ..................................... 23/253 R; 73/64.1
[58] Field of Search ........................ 23/253 R, 230 B; 73/64.1

[56] References Cited
U.S. PATENT DOCUMENTS

| 3,106,090 | 10/1963 | Barnes | 73/64.1 |
| 3,593,568 | 7/1971 | Schmitz et al. | 73/64.1 |

Primary Examiner—Robert M. Reese
Attorney, Agent, or Firm—Theodore B. Roessel; Roger Aceto

[57] ABSTRACT

Disclosed is a device for determining the activated clotting time of a blood sample, the device being a hand held unit for holding a glass tube containing the blood sample to be tested. The unit includes an electric heater for maintaining the blood sampe at 37° C and an electronic timer. A digital display on the unit can be selectively programmed to display either a temperature or a time function. Upon obtaining the desired temperature, the electronic timer is started and the blood sample is virtually observed in order to determine the elapsed time before the blood sample begins to clot.

11 Claims, 4 Drawing Figures

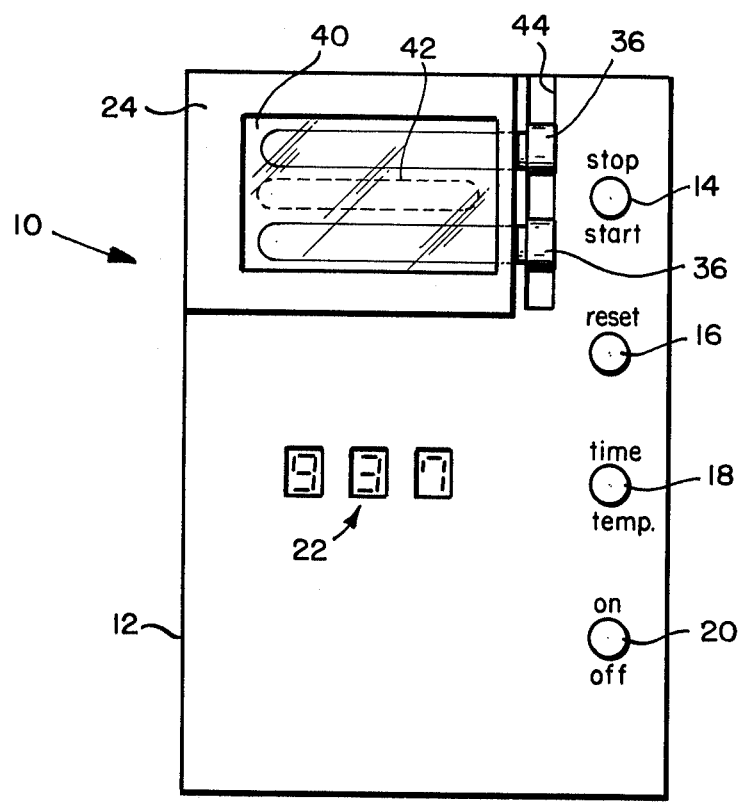
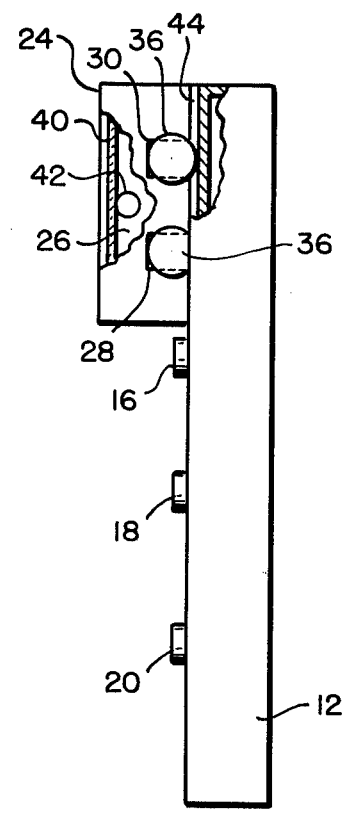
FIG. 1  FIG. 2
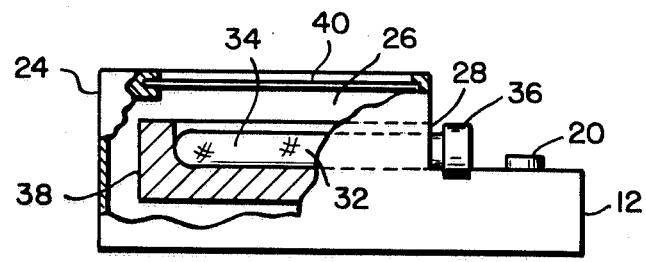
FIG. 3

DEVICE FOR DETERMINING THE ACTIVATED CLOTTING TIME OF A BLOOD SAMPLE

BACKGROUND OF THE INVENTION

The present invention relates generally to a device for determining the clotting time of whole blood and in particular to such a device which incorporates all the elements necessary to determine the clotting time into a compact hand held unit so as to permit the determination to be made at the patient's bedside.

The time it takes for whole blood to clot is an important factor in the conduct of various medical treatments or in the diagnosis of certain diseases. For example, knowledge of the clotting time of whole blood is essential for any patient undergoing heparin therapy which involves the administration of heparin to reduce the ability of the blood to clot. Such cases, for example, include patients undergoing treatment for thromboembolic disease or for those undergoing dialysis which involves the circulation of blood outside the body through a dialysis machine. The clotting time factor is also used in the diagnosis of certain diseases, such a hemophilia, Christmas disease and VonWillebrand's disease.

A general discussion of the technique for determining the clotting time of whole blood and its use in medical treatment and diagnosis is described generally in the American Journal of Clinical Pathology, volume 66, pages 899-940, 1976 and the Journal of the American Medical Association of May 2, 1966, volume 196 at pages 150-154. Briefly, the test involves the drawing of a small quantity (2 milliliters) of venous blood into a warmed tube containing diatomaceous earth. The tube is gently agitated to permit mixing and thereafter gently agitated at periodic intervals until the first definite clot is formed. The time interval between the appearance of blood in the tube and the first unmistakable clot is the activated coagulation time or the ACT. Throughout the entire procedure, the tube and its contents should be maintained at 37° C.

Heretofore, the equipment used to perform the test consisted of a water bath or preheated block, a timer calibrated in one second intervals and a thermometer. All this equipment made the test awkward if not difficult to perform at the patient's bedside. In addition, the need for periodically withdrawing the tube from the bath or heat block to inspect for clots detracted from the maintenance of the desired temperature of the samples throughout the test procedure. Also, just when the first definitive clot begins to form is a subjective determination which could be facilitated by continuous observation of the sample. However, equipment heretofore used did not make such continuous observation possible in that if either a heating block or water bath is used, the sample must be removed to inspect for clots and then returned in order to maintain the sample at temperature.

The present invention, in contrast to prior apparatus used, provides a portable unit to perform the test wherein the unit is capable of performing the heating and timing function of the test while allowing continuous observation of the sample. All these functions are incorporated into a hand held unit which permits the test to be conveniently conducted at the patient's bedside and which permits the sample to be agitated as required by the test.

SUMMARY OF THE INVENTION

The present invention can be characterized in one aspect thereof by the provision of a hand held housing defining a chamber for receiving a glass tube containing the blood sample to be tested, the housing having a window portion to permit visual observation of the sample; a heater in the housing for maintaining the temperature of the sample at 37° C; an electronic counter; a display on the housing for reading the contents of the counter as a time function; and means for starting and stopping the display without interrupting the operation of the counter so that restarting the display from a stop condition produces a readout on the display representing the sum of previous readout plus the elapsed count since the last stop condition.

DESCRIPTION OF THE DRAWINGS

FIG. 1 is a plan view of the unit of the present invention;
FIG. 2 is a side elevation view of the unit;
FIG. 3 is an end elevation view of the unit partly broken away in section.

DESCRIPTION OF THE PREFERRED EMBODIMENTS

Figure 4:
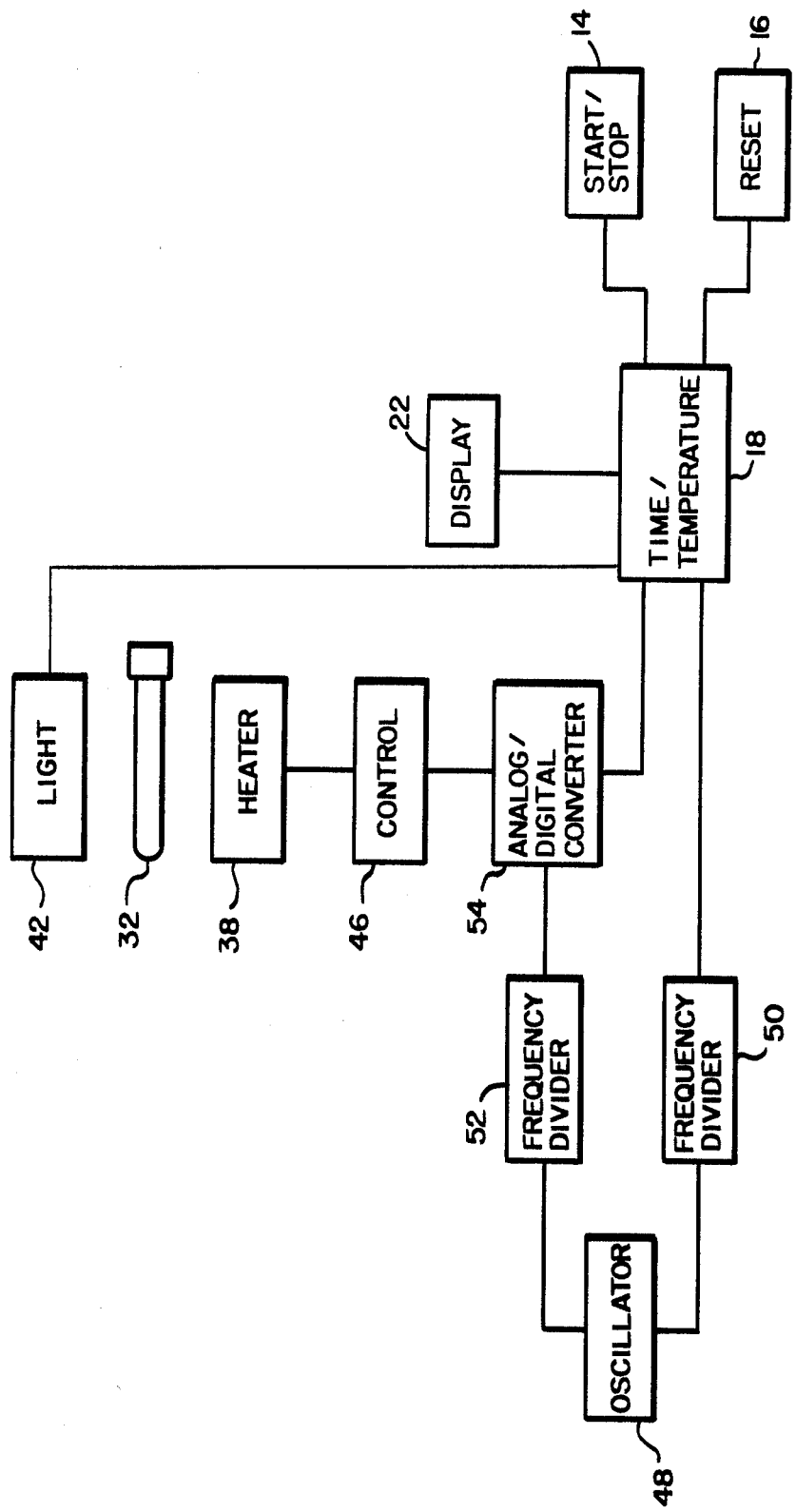
FIG. 4 is a block diagram of the electronics within the unit.

Referring to the drawings, FIG. 1 shows the testing unit of the present invention generally indicated at 10. The unit includes a housing 12 which contains the electronic components schematically diagramed in FIG. 4. The housing also contains the power supply (not shown) such as a battery or the like for operating the unit. The unit is of a size which can be conveniently held in one hand with the overall length being approximately 7 inches and the width 5 inches. Arranged along the right hand side of housing 12 as viewed in FIG. 1 are four push button keys for operating the unit as set out hereinbelow, including a stop/start key 14, a reset key 16, a time/temperature key 18 and an on/off key 20.

Centrally located on the face of housing 12 is a digital read-out 22 wherein the time or temperature functions are displayed.

As shown in the figures, housing 12 has adjacent one end an upstanding portion 24. This portion defines a chamber 26 (FIGS. 2 and 3) with two openings 28, 30 for receiving therein, two glass tubes 32. The glass tube inserted through opening 28 will eventually receive the sample of blood to be tested whereas the other tube is used as a reserve for subsequent tests. Tubes 32 are standard articles of commerce and form no part of the present invention. For example, one tube suitable for use in the test procedure is sold by the Becton, Dickinson and Company under the trademark VACUTAINER. It is sufficient for purposes of the present invention merely to say that such tubes include a glass body 34 and a rubber stopper 36. Each tube is pre-sterilized and is evacuated to facilitate the drawing of venous blood into the tube. The tubes, as sold, also contain the appropriate amount of diatomaceous earth or the like required in performing the test and are of a size sufficient to hold the amount of blood required in the test, namely, approximately 2ml.

Within chamber 26, is a heating block 38 designed to receive the body of each glass tube. The contours of the heating block are designed for close, intimate contact with the glass body 34 of each tube to insure a good transfer of heat between the heating block and the tubes.

Upstanding portion 24 is also provided with a window 40 so that glass tubes 32 and their contents can be observed without removing the tube from the heating block. To further facilitate observation of the contents of the particular glass tube holding the blood sample, chamber 26 is provided with a light source 42 (FIGS. 1 and 2) which illuminates the portion of the chamber containing the glass tube inserted through opening 28.

Completing the structure of housing 12 is a channel or groove 44 which passes along upstanding portion 24 adjacent the openings 28, 30 into chamber 26. The purpose of this groove is to receive and frictionally hold the rubber stopper 36 of each glass tube. This acts as a clamping means to hold the glass tube in chamber 26 as the unit 10 is periodically tilted in accordance with the test procedure.

Referring now to the block diagram of FIG. 4, the electrical components within housing 12 include a control circuit 46. The electronic components making up control circuit 46 would include for example, any suitable temperature sensor, temperature reference and comparator so as to maintain heater 38 slightly above 37° C. The electronics also include an oscillator 48 having its output directed to either of two frequency dividers 50 and 52. The oscillator and frequency divider 50 together with a counter (not shown) act as an electronic clock to perform the timing function of the ACT test. This time function can be shown on display 22 by operation of time/temperature key 18 and its associated circuitry. The other frequency divider is used with an analog-to-digital converter 54 to digitize the output of temperature control circuit 46. This information can thus be shown on display 22 as the temperature function of the ACT test by operation of the temperature key. Thus, the time/temperature key 18 and its associated circuitry can be operated to selectively show either the time or temperature of the test on digital display 22.

While there is relatively good heat transfer between heating block 38 and glass tubes 32, there does exist a temperature gradient between them over the heating range. It has been empirically determined that this gradient is about 1° C. The analog-to-digital converter 54 includes a compensating feature operating over the heating range which takes this temperature gradient into consideration so that the temperature read out appearing on digital display 22 is slightly below the actual temperature of the heating block. For example, when display 22 shows a temperature of 37° C, the actual temperature of the heating block would be about 38° C.

When the components making up the electronic clock are connected to the digital display, start/stop switch 14 and its associated circuitry can be operated to inactivate the ability of the display to read the clock. However, operation of the start/stop switch stops only the read-out function and does not stop the operation of the clock itself. Thereafter, pressing the start/stop switch 14 again, will result in the display indicating the sum of the previous display plus the elapsed time since the stop condition was activated. Thus, start/stop switch 14 and its associated circuitry will provide a time update feature so that the display itself may be started and stopped several times, without interferring with the continuous running the electronic clock. Resetting the clock to zero is accomplished by reset key 16 and its associated circuitry.

In operation, the on/off key 20 is pushed to activate the power supply of the unit such as a battery or other DC source (not shown). This supplies power to heater control 46 to begin heating heater block 38 up to the operating temperature. At the same time, the digital display 22 is lit and indicates the temperature of the heating block. In approximately 15 minutes, the display will indicate that the temperature of heater block 38 has reached 37° C. At this point, one or two empty glass tubes 32 are inserted into chamber 26 through housing openings 28 and 30. The rubber stoppers 36 of each tube are pressed firmly in groove 40 so as to clamp the tubes in the chamber and in direct contact with heater block 38.

It takes approximately 3 minutes for the empty glass tubes to reach the temperature of 37° C. Accordingly, when the tubes are put in place, the time/temperature key temperature button 18 can be pushed to start the clock and display the contents of the clock on digital display 22. Pushing key 18 also turns on light 42 to facilitate observation of the tube inserted through opening 28. Display 22 indicates time in seconds, so when it reads 180, the operator can be reasonably assured that the glass tubes are at the proper temperature of 37° C. At this point, the venous blood specimen is collected and drawn directly from the patient into the prewarmed glass tube. When the blood sample first enters the tube, the timing sequence of the test can be initiated by pressing and immediately releasing reset button 16. This resets and starts electronic clock at zero.

According to the standard test technique, the glass tube containing the blood sample should be inverted five times after it is filled to insure the proper mixing of the materials in the tube with the blood sample. This can be done either by removing the glass tube from the unit or simply by inverting the entire unit the required number of times. At the 60 second mark, and at 5 second intervals thereafter, the unit is gently tilted from side to side and the sample observed through window 40 to detect the appearance of the first visible clot. When the clot is detected, stop/start key 14 is pressed which stops the display. However, in the event that further observation of the sample indicates that the end point determination was premature, i.e. a clot actually begins forming say 10 seconds later than the point at which the timer was stopped, the start/stop key can be depressed and released twice in succession. Since the electronic clock mechanism continues to run, this will update the display to indicate the actual total elapsed time from the start of the procedure. At this point, the time/temperature key 18 can be pushed to reconnect heater control 46 to the display to reconfirm that the temperature of the heater block is still at 37° C. If for any reason another test is to be rerun to confirm the results of the previous test, the reserve glass tube in opening 30 is at temperature and readily available for use.

Thus it should be appreciated that the present invention provides all the elements needed to perform the ACT test in a single hand held unit. The unit provides for the incubation of the sample at 37° C and illumination to aid in clot detection, the required timing capacity and a digital display to selectively indicate either incubation temperature or elapsed time. The unit further provides the capability of compensating for any error due to a premature determination of clot formation by providing the means to update the time function of the test. The design also permits glass tubes 32 to be clamped within the housing in a manner which does not in anyway interfere with the drawing of the blood sample into the tubes.

Having described the invention in detail, what is claimed as new is:

1. A device for determining the activated coagulation time of whole blood comprising:
   (a) a hand held housing;
   (b) an upstanding portion on said housing defining a chamber for receiving a rubber capped glass tube containing a sample of blood to be tested;
   (c) said upstanding portion having a window to observe the tube in said chamber;
   (d) an electric heater in said housing for maintaining the glass tube and blood sample at substantially 37° C;
   (e) a timer in said housing; and
   (f) means on said housing to manually start said timer when a blood sample enters the tube and to stop said timer when a clot is observed to form in the blood sample.

2. A device as in claim 1 wherein said housing has a groove adjacent said upstanding portion adapted to receive the rubber cap of the glass tube for clamping the tube in said chamber.

3. A device as in claim 1 including:
   (a) an oscillator in said housing;
   (b) a first frequency divider which together with said oscillator defines said timer;
   (c) a control circuit to maintain said heater at about 37° C, said control circuit producing an analog output signal representing the temperature of said heater;
   (d) an analog-to-digital converter for transforming said analog output signal to a digital signal; and
   (e) a second frequency divider which together with said oscillator drives said analog-to-digital converter.

4. A device as in claim 3 including a digital display on said housing and means to selectively display either the temperature of said heater or the contents of said timer on said digital display.

5. A device for determining the activated coagulation time of whole blood comprising:
   (a) a hand held housing provided with a chamber for receiving a glass tube containing a sample of the blood to be tested;
   (b) electric heater means in said chamber for maintaining the temperature of the tube and blood sample therein at substantially 37° C;
   (c) an electronic clock in said housing;
   (d) digital display means on said housing for reading out the contents of said clock;
   (e) a start/stop circuit in said housing operatively connected to said display means for selectively starting and stopping said display means while said electronic clock continues to operate, said circuit when restarting said display means producing a read out on said display means which represents the sum of the previous read-out plus the elapsed time since the last stop condition; and
   (f) means for resetting said electronic clock to zero.

6. A device as set forth in claim 5 wherein said housing has a window to facilitate observation of a tube and blood sample in said chamber.

7. A device as set forth in claim 5 including clamp means on said housing for holding a glass tube in said chamber.

8. A device as set forth in claim 7 wherein said clamp means is a groove on said housing adjacent said chamber, said groove being adapted to receive therein a rubber cap used to seal the tube containing the blood sample.

9. A device as in claim 5 wherein said heater means comprises:
   (a) a heating block in said chamber;
   (b) control means maintaining said heating block at 37° C and issuing a signal representing the temperature of said block; and
   (c) an analog/digital converter to digitize said signal and calibrated to display on said digital display means the temperature of the blood sample being tested.

10. A device as in claim 9 including a time/temperature key on said housing operatively connected to said electronic clock, said analog/digital converter and said display, said key being operable to selectively connect either said clock or said converter to said display.

11. A device as in claim 9 wherein said electronic clock includes an oscillator and a first frequency divider, said oscillator and a second frequency divider driving said analog/digital converter.

* * * * *